(12) United States Patent
Farley et al.

(10) Patent No.: US 9,433,758 B2
(45) Date of Patent: Sep. 6, 2016

(54) INTRAVASCULAR CATHETER INSERTION DEVICE

(71) Applicants: Sean S. Farley, Hidden Hills, CA (US); Boris Ratiner, Hidden Hills, CA (US)

(72) Inventors: Sean S. Farley, Hidden Hills, CA (US); Boris Ratiner, Hidden Hills, CA (US)

( * ) Notice: Subject to any disclaimer, the term of this patent is extended or adjusted under 35 U.S.C. 154(b) by 98 days.

(21) Appl. No.: 14/326,088

(22) Filed: Jul. 8, 2014

(65) Prior Publication Data

US 2015/0018769 A1 Jan. 15, 2015

Related U.S. Application Data

(60) Provisional application No. 61/844,349, filed on Jul. 9, 2013.

(51) Int. Cl.
 *A61M 25/06* (2006.01)
(52) U.S. Cl.
 CPC ...... *A61M 25/0606* (2013.01); *A61M 25/0693* (2013.01)
(58) Field of Classification Search
 CPC ............... A61M 25/0606; A61M 25/0693; A61M 5/3271
 USPC .......... 604/143, 144, 164.02, 164.08, 164.12
 See application file for complete search history.

(56) References Cited

U.S. PATENT DOCUMENTS

| | | | |
|---|---|---|---|
| 4,487,605 A | 12/1984 | McGaughey | |
| 4,906,236 A | 3/1990 | Alberts | |
| 4,944,728 A | 7/1990 | Carrell | |
| 4,966,589 A | 10/1990 | Kaufman | |
| 5,186,712 A | 2/1993 | Kelso | |
| 5,195,985 A | 3/1993 | Hall | |
| 5,300,046 A | 4/1994 | Scarfone | |
| 5,312,361 A | 5/1994 | Zadini | |
| 5,334,159 A | 8/1994 | Turkel | |
| 5,336,176 A | 8/1994 | Yoon | |
| 5,407,431 A | 4/1995 | Botich | |
| 5,411,486 A | 5/1995 | Zadini | |
| 5,415,177 A | 5/1995 | Zadini | |
| 5,423,760 A | 6/1995 | Yoon | |
| 5,423,770 A | 6/1995 | Yoon | |
| 5,480,388 A | 1/1996 | Zadini et al. | |
| 5,527,290 A | 6/1996 | Zadini et al. | |
| 5,527,291 A | 6/1996 | Zadini | |
| 5,591,138 A * | 1/1997 | Vaillancourt ....... | A61M 5/3271 604/192 |
| 5,676,658 A | 10/1997 | Erskine | |
| 5,690,619 A | 11/1997 | Erskine | |
| 5,700,250 A | 12/1997 | Erskine | |

(Continued)

*Primary Examiner* — Kevin C Sirmons
*Assistant Examiner* — Leah Swanson
(74) *Attorney, Agent, or Firm* — Hackler Daghighian Martino & Novak

(57) ABSTRACT

A catheter insertion device has a generally hollow housing having a closed base end opposite an open distal end. A hollow needle defines a channel in fluidic or pneumatic communication between a distal skin-piercing end and the proximal needle end. A plunger is slidably disposed over at least a portion of the hollow needle. The distal skin-piercing end of the hollow needle extends through the plunger distal end. An expandable chamber is at least partially formed by the plunger proximal chamber end and at least an inside surface of the closed based end of the generally hollow needle, where the expandable chamber is in fluidic or pneumatic communication with the channel of the hollow needle through the proximal needle end. The expandable chamber is configured to increase in volume as the plunger moves towards the distal skin-piercing end of the hollow needle.

26 Claims, 15 Drawing Sheets

(56) References Cited

U.S. PATENT DOCUMENTS

| | | |
|---|---|---|
| 5,749,371 A | 5/1998 | Zadini |
| 5,749,856 A | 5/1998 | Zadini |
| 5,755,709 A | 5/1998 | Cuppy |
| 5,795,339 A | 8/1998 | Erskine |
| 5,865,806 A | 2/1999 | Howell |
| 5,879,337 A | 3/1999 | Kuracina |
| 5,879,338 A | 3/1999 | Mahurkar |
| 5,911,705 A | 6/1999 | Howell |
| 6,001,080 A | 12/1999 | Kuracina |
| 6,086,563 A | 7/2000 | Moulton |
| 6,090,078 A | 7/2000 | Erskine |
| 6,165,136 A | 12/2000 | Nishtala |
| 6,197,001 B1 | 3/2001 | Wilson |
| 6,210,375 B1 | 4/2001 | Moulton |
| 6,217,558 B1 | 4/2001 | Zadini |
| 6,273,861 B1 | 8/2001 | Bates |
| 6,277,100 B1 | 8/2001 | Raulerson |
| 6,280,401 B1 | 8/2001 | Mahurkar |
| 6,287,322 B1 | 9/2001 | Zhu |
| 6,379,337 B1 | 4/2002 | Mohammad |
| 6,398,743 B1 | 6/2002 | Halseth |
| 6,443,929 B1 | 9/2002 | Kuracina |
| 6,582,402 B1 | 6/2003 | Erskine |
| 6,626,859 B2 | 9/2003 | von Segesser |
| 6,629,959 B2 | 10/2003 | Kuracina |
| 6,786,875 B2 | 9/2004 | Barker |
| 6,796,963 B2 | 9/2004 | Carpenter |
| 6,835,193 B2 | 12/2004 | Epstein |
| 6,860,871 B2 | 3/2005 | Kuracina |
| 6,878,129 B2 | 4/2005 | Donaldson |
| 6,979,317 B2 | 12/2005 | Galt |
| 7,153,276 B2 | 12/2006 | Barker |
| 7,294,118 B2 | 11/2007 | Saulenas |
| 7,344,516 B2 | 3/2008 | Erskine |
| 7,422,572 B2 | 9/2008 | Popov |
| 7,481,797 B2 | 1/2009 | Mahurkar |
| 7,534,231 B2 | 5/2009 | Kuracina |
| 7,691,083 B2 | 4/2010 | Botich |
| 7,731,692 B2 | 6/2010 | Moos |
| 7,846,132 B2 | 12/2010 | Gravesen |
| 7,850,650 B2 | 12/2010 | Breitweiser |
| 7,927,314 B2 | 4/2011 | Kuracina |
| 7,967,776 B2 | 6/2011 | von Segesser |
| 8,062,261 B2 | 11/2011 | Adams |
| 8,133,237 B2 | 3/2012 | Oostman, Jr. |
| 8,157,835 B2 | 4/2012 | Taylor |
| RE43,473 E | 6/2012 | Newby |
| 8,292,849 B2 | 10/2012 | Bobroff |
| 8,308,685 B2 | 11/2012 | Botich |
| 8,313,493 B2 | 11/2012 | Fischer |
| 8,414,539 B1 | 4/2013 | Kuracina |
| 8,444,605 B2 | 5/2013 | Kuracina |
| 2003/0028172 A1 | 2/2003 | Epstein |
| 2003/0120223 A1 | 6/2003 | Von Segesser |
| 2004/0116855 A1 | 6/2004 | Popov |
| 2006/0184105 A1 | 8/2006 | Townsend |
| 2010/0004558 A1 | 1/2010 | Frankhouser |
| 2010/0010499 A1 | 1/2010 | Fischer |
| 2011/0166526 A1 | 7/2011 | Kuracina |
| 2012/0016307 A1 | 1/2012 | Burkholz |
| 2012/0209303 A1 | 8/2012 | Frankhouser |
| 2012/0238966 A1 | 9/2012 | Kuracina |
| 2013/0066200 A1 | 3/2013 | Frankhouser |

* cited by examiner

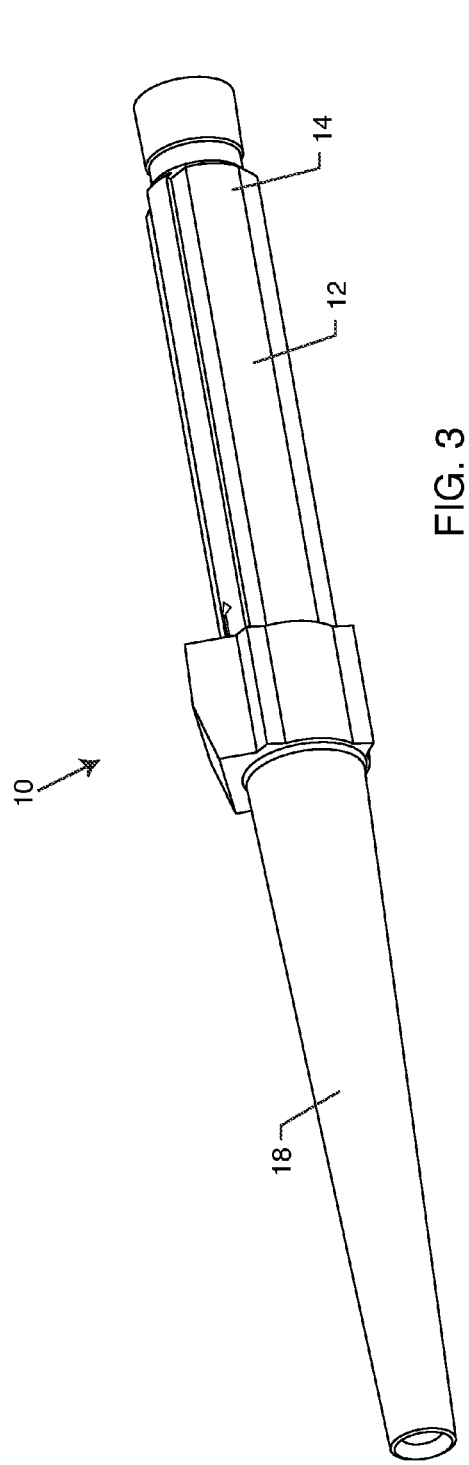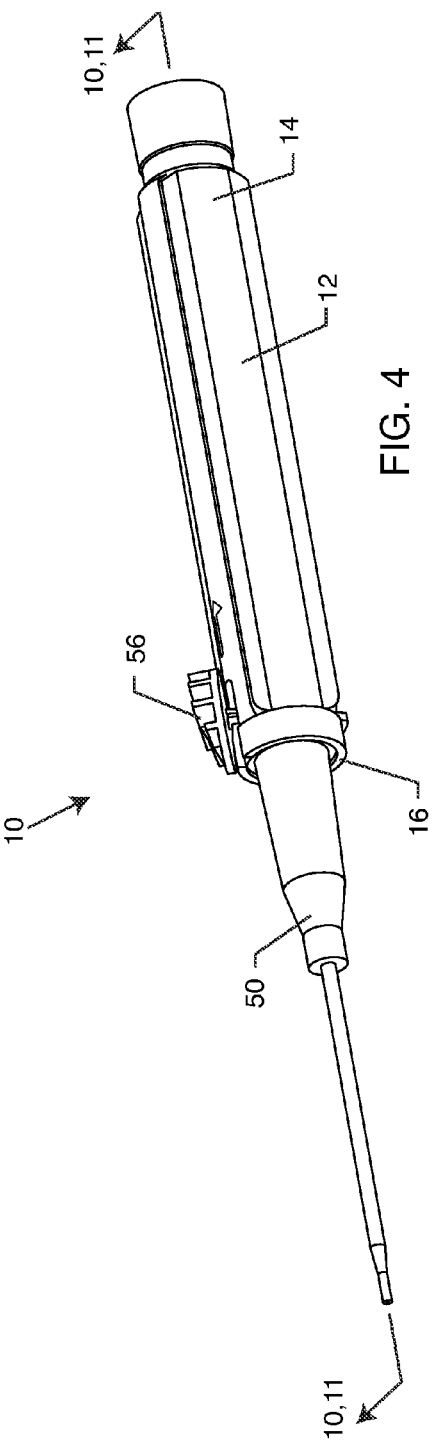

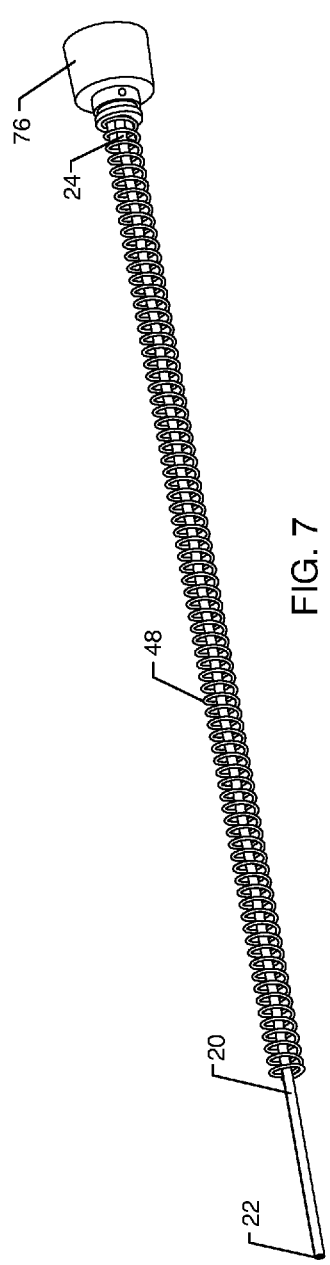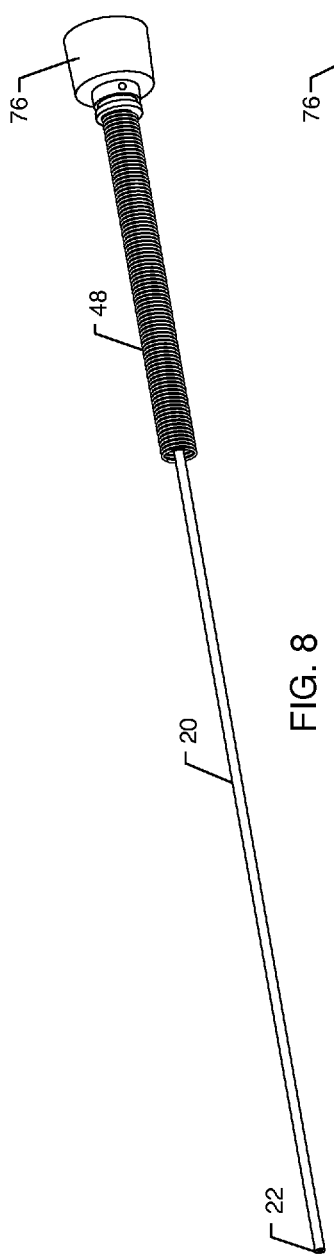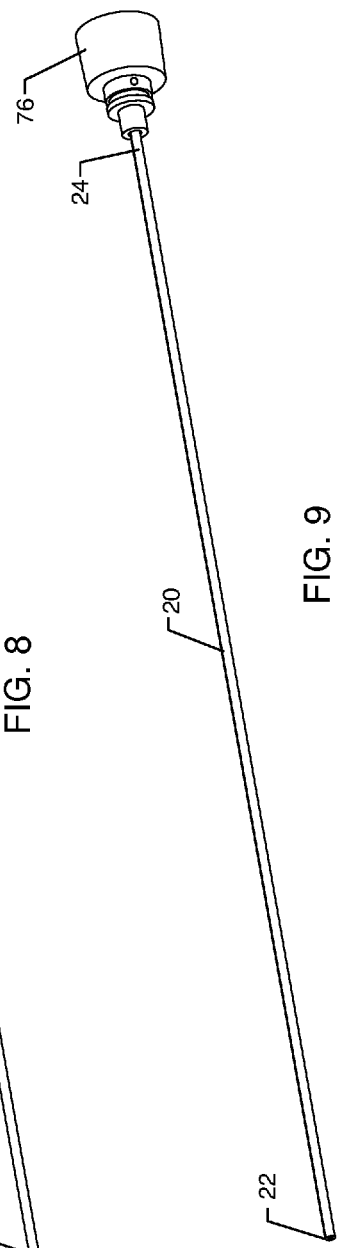

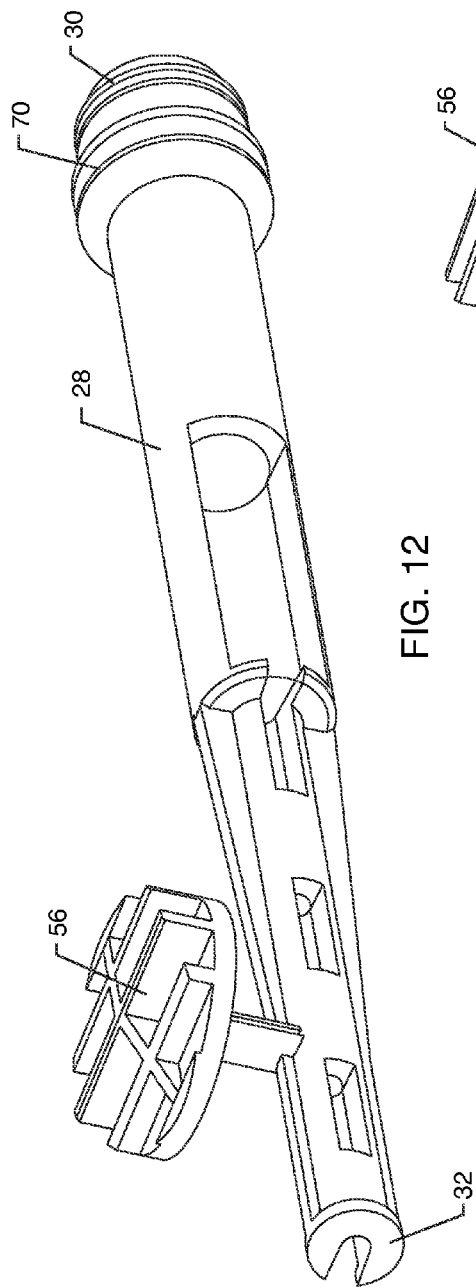
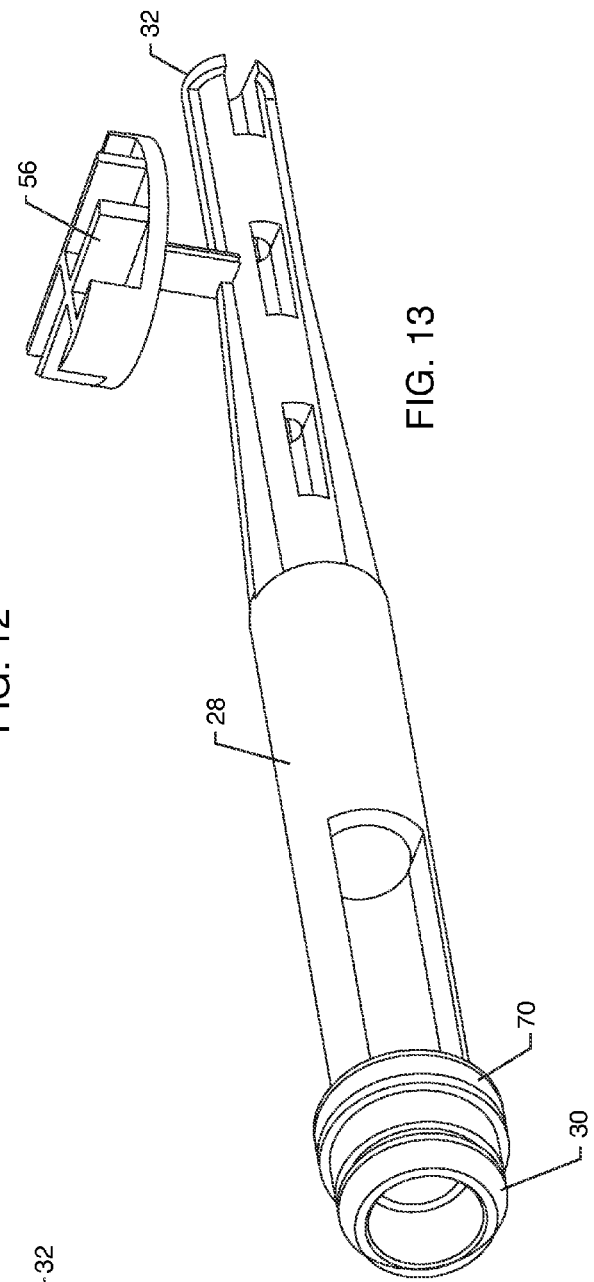

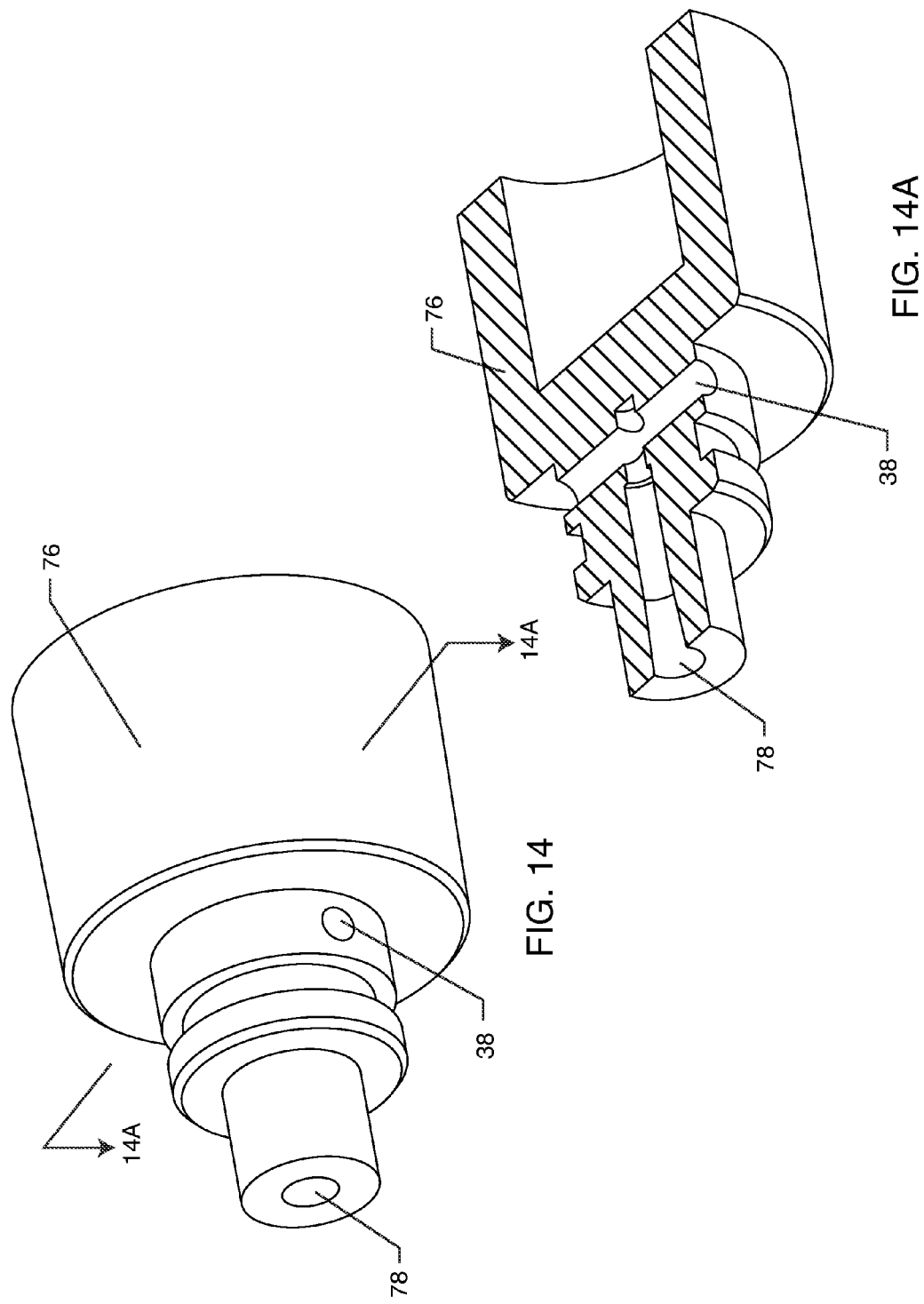

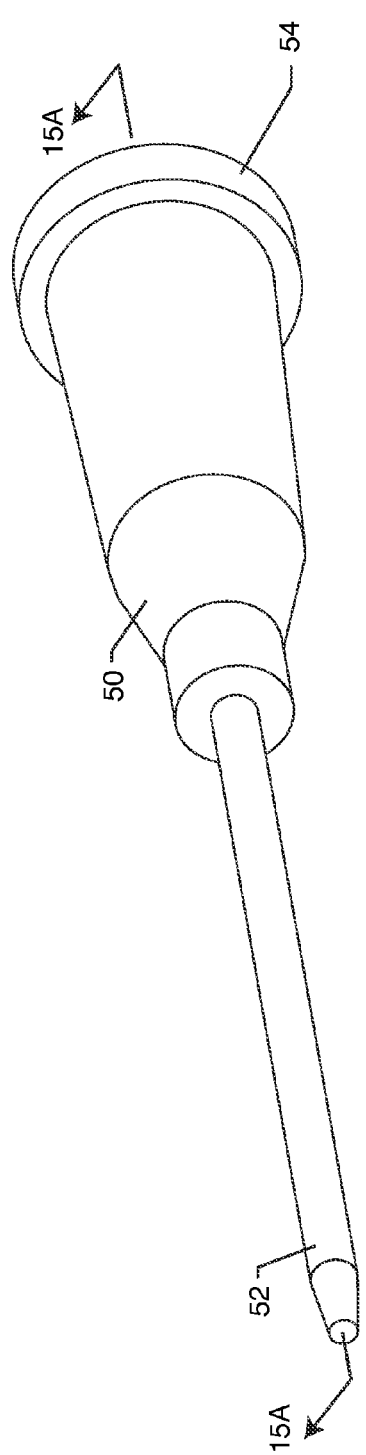
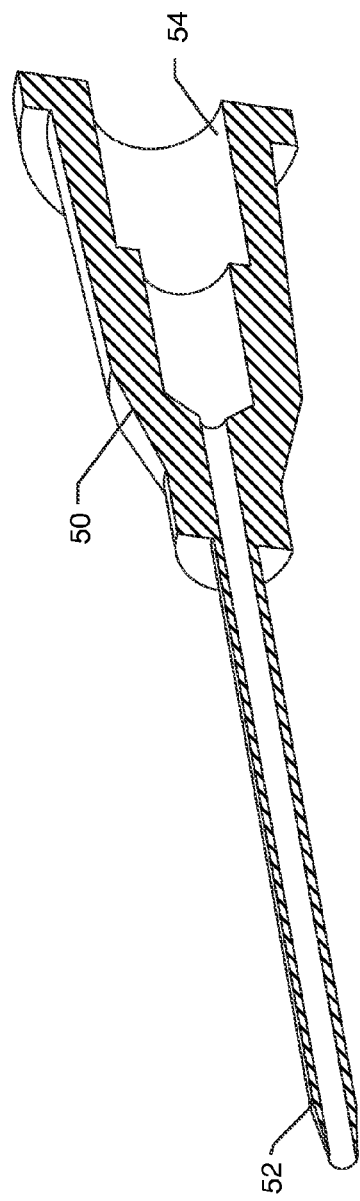
FIG. 15
FIG. 15A

INTRAVASCULAR CATHETER INSERTION DEVICE

CROSS-REFERENCE TO RELATED APPLICATIONS

This non-provisional application claims priority to provisional application 61/844,349 filed on Jul. 9, 2013, the entire contents of which are hereby fully incorporated by this reference.

DESCRIPTION

1. Field of the Invention

The present invention generally relates to intravascular catheters. More particularly, the present invention relates to an intravascular catheter insertion device that automatically inserts a catheter upon a vacuum seal being broken that utilizes just one spring and two seals. Furthermore, this particular embodiment is configured to remove or reduce stiction and is reloadable.

2. Background of the Invention

Properly inserting a catheter into a vein or artery is a very difficult process. It is not always easy for a technician, nurse or doctor to properly locate a vein or artery. Furthermore, it is also difficult to know how much pressure to apply to the needle. Many people have different densities of body tissue. Body tissue density can also change with a person's age. On top of these problems, the vein or artery the technician is trying to reach cannot be punctured on both sides. The vein may be very thins and it is easy to go through both sides of a vein. If the vein or artery is pierced on both sides it is no longer a proper vein or artery to use for the intended purpose. The technician must repeat the process adding significant discomfort and pain into the patient.

Typically, proper insertion of a catheter takes years of trial and error and skill. However, even the most experienced technicians, nurses or doctors are not able to consistently insert a catheter on the first try especially under stress or unstable conditions. Accordingly, there is a need for a new device that removes much of the guess work and skill of inserting a catheter into the vein or artery. The present invention fulfills these needs and provides other related advantages by inserting the catheter when the first side of a vein is pierced but before the second side of the vein is pierced.

SUMMARY OF THE INVENTION

An exemplary embodiment of a catheter insertion device includes a hollow needle having a distal skin-piercing end opposite a proximal base end. The hollow needle defines a channel in fluidic or pneumatic communication between the distal skin-piercing end and the proximal base end. A plunger is slidably disposed over at least a portion of the hollow needle, where the distal skin-piercing end of the hollow needle extends through a distal end of the plunger. A spring is mechanically engaged between at least a portion of the proximal base end of the hollow needle and a portion of the plunger. The spring biases the plunger towards the distal skin-piercing end of the hollow needle. A catheter is slidably disposed over at least a second portion of the hollow needle where the distal skin-piercing end of the hollow needle extends through a distal insertion end of the catheter. The catheter includes the distal insertion end opposite a proximal connection end, where the proximal connection end of the catheter is configured to be disposed next to the distal end of the plunger. An expandable chamber has a first opening in fluidic or pneumatic communication with the channel of the hollow needle. The expandable chamber is at least partially formed by the proximal base end of the hollow needle and a proximal end of the plunger. The expandable chamber is configured to increase in volume as the plunger moves towards the distal skin-piercing end of the hollow needle.

In other exemplary embodiments a first circumferential seal of the expandable chamber may be disposed about the proximal base end of the hollow needle. The first circumferential seal may be configured to seal the proximal base end to the plunger when the plunger is moved to its furthest proximal position. A second circumferential seal of the expandable chamber may be disposed about the plunger, the second circumferential seal configured to seal the plunger to the housing when the plunger is moved to its furthest proximal position. A button may be non-movably attached to the plunger and extending outside of the housing. The seals can be either separate O-rings or separate seals, or alternatively, could be part of the structure and molded into the housing or plunger.

In other exemplary embodiments a housing may be attached to the proximal base end of the hollow needle. The housing may include a J-shaped slot, where the button is configured to be moveable within the J-shaped slot between a stored position, an armed position and an extended position. The stored position is when the button is located at a lower end of the J-shaped slot. The armed position is when the plunger is moved to its furthest proximal position or to a more proximal position. The extended position is when the plunger is moved to its furthest distal position. When in the armed position a small gap may be disposed between the proximal connection end of the catheter and the distal end of the plunger. This also allows the device to be reloadable as a medical technician can reload the device manually.

In other exemplary embodiments the plunger may include a circumferential recess and the housing may include a needle guard flexure having a distal engagement tip. When the plunger is in the extended position the distal engagement tip of the housing is captured within the circumferential recess of the plunger and the plunger is fixedly secured in relation to the hollow needle. The distal end of the plunger is then beyond the distal skin-piercing end of the hollow needle.

The first and second circumferential seals may be each configured to abut only one of either the plunger or the housing when the plunger is in the extended position and stored position.

The expandable chamber may have a substantially zero volume when the plunger is in the armed position.

Another exemplary embodiment of a catheter insertion device has a generally hollow housing having a closed base end opposite an open distal end. A hollow needle has a distal skin-piercing end opposite a proximal needle end. The distal skin-piercing end would typically have a sharp beveled end that is designed to easily penetrate bodily tissue such as the skin. The proximal needle end is non-movably attached to the closed base end of the generally hollow housing and the proximal needle end is disposed within the generally hollow housing. The distal skin-piercing end of the hollow needle extends beyond the open distal end of the generally hollow housing. The hollow needle defines a channel in fluidic or pneumatic communication between the distal skin-piercing end and the proximal needle end. A plunger is slidably disposed over at least a portion of the hollow needle. The plunger includes a plunger proximal chamber end opposite a plunger distal end. The distal skin-piercing end of the hollow needle extends through the plunger distal end. An expandable chamber is at least partially formed by the plunger proximal chamber end and at least an inside surface of the closed based end of the generally hollow needle, where the expandable chamber is in fluidic or pneumatic communication with the channel of the hollow needle through the proximal needle end. The expandable chamber is configured to increase in volume as the plunger moves towards the distal skin-piercing end of the hollow needle. A first seal is attached to either an inside surface of the plunger or the generally hollow housing. A second seal is attached to either an outside surface of the plunger and the generally hollow housing. The first seal is configured to seal between the inside surface of the plunger and the generally hollow housing when the plunger is at its furthest proximal position and the second seal is configured to seal between the outside surface of the plunger and the generally hollow housing when the plunger is at its furthest proximal position. A spring is mechanically engaged between the generally hollow housing and the plunger. The spring biases the plunger towards the distal skin-piercing end of the hollow needle. A catheter is slidably disposed over at least a second portion of the hollow needle where the distal skin-piercing end of the hollow needle extends through a distal insertion end of the catheter. The catheter includes the distal insertion end opposite a proximal connection end, where the proximal connection end of the catheter is configured to be disposed next to the plunger distal end.

In other exemplary embodiments a button may be non-movably attached to the plunger and extends outside of the generally hollow housing. The housing may include a J-shaped slot, where the button is configured to be moveable within the J-shaped slot between a stored position, an armed position and an extended position. The stored position is when the button is located at a lower end of the J-shaped slot. The armed position is when the plunger is moved to its furthest proximal position. The extended position is when the plunger is moved to its furthest distal position. The armed position has a small gap is disposed between the proximal connection end of the catheter and the plunger distal end.

The plunger may have a circumferential recess where then the generally hollow housing has a needle guard flexure having a distal engagement tip, wherein when the plunger is in the extended position the distal engagement tip of the generally hollow housing is captured within the circumferential recess of the plunger. The plunger is then fixedly secured in relation to the hollow needle. The plunger distal end is positioned beyond and covers the distal skin-piercing end of the hollow needle.

The first and second circumferential seals may each be configured to abut only one of either the plunger or the housing when the plunger is in the stored and extended position.

The proximal connection end of the catheter may engage the open distal end of the generally hollow housing, where movement of the catheter towards the closed base end of the generally hollow housing is prevented when the plunger moves towards the closed base end of the generally hollow housing when the plunger moves from the stored position to the armed position.

Another exemplary embodiment of a catheter insertion device includes an elongated hollow needle having a distal skin-piercing end opposite a proximal needle end. The proximal needle end is non-movably fixed to a needle base, where the elongated hollow needle defines a channel in fluidic or pneumatic communication between the distal skin-piercing end and the proximal needle end. A generally hollow housing has an open distal end opposite a housing proximal end. The needle base is non-movably attached to the housing proximal end. A plunger is translatably disposed over at least a portion of the elongated hollow needle, where the distal skin-piercing end extends through a plunger distal end. A spring is mechanically engaged between the plunger and either the housing proximal end or the needle base. The spring is configured to bias the plunger towards the distal skin-piercing end. A catheter is translatably disposed over at least a second portion of the elongated hollow needle. The catheter includes a distal insertion end opposite a proximal connection end, where the distal skin-piercing end extends through the distal insertion end of the catheter. The proximal connection end of the catheter is configured to be disposed next to the plunger distal end. An expandable chamber is formed by a proximal plunger end of the plunger, an outside surface of the needle base and an inside surface of the housing proximal end. The expandable chamber varies in volume according to translational movement of the plunger. A first seal is disposed around the outside surface of the needle base and a second seal is disposed around an outside surface of the plunaer.

In other exemplary embodiments the plunger may be manually moveable between a stored position and an armed position, where the armed position includes the chamber having a substantially zero (or very low) volume as the plunger is in its furthest proximal position. When the plunger is in the armed position, the first seal may be disposed between the outside surface of the needle base and an inside surface of the plunger, and the second seal may be disposed between the outside surface of the plunger and the inside surface of the housing proximal end.

Another exemplary embodiment of a catheter insertion device includes a generally hollow housing having an open distal end opposite a housing base end. A hollow needle has a distal skin-piercing end opposite a proximal needle end. The hollow needle defines a channel in fluidic or pneumatic communication between the distal skin-piercing end and the proximal needle end. The proximal needle end is non-movably attached to the housing base end and the distal skin-piercing end of the hollow needle extends beyond the open distal end of the generally hollow housing. A plunger is slidably disposed over at least a portion of the hollow needle. The plunger includes a plunger proximal end opposite a plunger distal end, where the distal skin-piercing end of the hollow needle extends through the plunger distal end. A spring is mechanically engaged between the generally hollow housing and the plunger. The spring biases the plunger towards the distal skin-piercing end of the hollow needle. An expandable chamber is defined at least partially by the plunger proximal end and an inside surface of the housing base end. The expandable chamber is in fluidic or pneumatic communication with the channel of the hollow needle, where the expandable chamber is configured to increase in volume when the vacuum is broken and the plunger move towards the distal skin-piercing end of the hollow needle.

In other exemplary embodiments a first seal may be disposed between an outside surface of the plunger and the housing base end. A second seal may be disposed between an inside surface of the plunger and the housing base end. A catheter may be slidably disposed over at least a second portion of the hollow needle where the distal skin-piercing end of the hollow needle extends through a distal insertion end of the catheter. The catheter may include the distal insertion end opposite a proximal connection end, where the proximal connection end of the catheter is configured to be disposed next to the plunger distal end.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 3 is another perspective view of the exemplary embodiment of FIG. 1;

FIG. 4 is a perspective view similar to FIG. 3 now with the cap removed;

FIG. 7 is a perspective view similar to FIG. 6 now with the plunger removed and showing the spring in the extended position;

FIG. 8 is a perspective view similar to FIG. 7 now with the spring shown in the armed or stored position;

FIG. 9 is a perspective view similar to FIG. 7 or 8 now with the spring removed;

FIG. 12 is a perspective view of the plunger from FIGS. 1-11;

FIG. 13 is another perspective view of the plunger from FIGS. 1-11;

FIG. 14 is a perspective view of an exemplary needle base of the structure of FIGS. 1-13;

FIG. 14A is a sectional view taken along lines 14A-14A from FIG. 14;

FIG. 15 is a perspective view of an exemplary catheter of the structure of FIGS. 1-14;

FIG. 15A is a sectional view taken along lines 15A-15A from FIG. 15;

DETAILED DESCRIPTION OF THE PREFERRED EMBODIMENTS

This application discloses a new method and structure of inserting an intravascular (IV) catheter into the organic tissue, such as inserting an IV catheter into a vein or artery for blood withdrawal. This novel invention dramatically simplifies prior catheter designs (such as U.S. Pat. Nos. 5,313,361 and 5,480,388 and 5,527,290 which are fully incorporated herein with this reference) and dramatically increases the ability to properly insert the needle into a vein or artery.

This invention utilizes a single spring to create a vacuum chamber. When the needle is inserted under the skin, a spring is released and biases a plunger to move forward. However, the plunger doesn't move forward because it is held back due to a vacuum chamber formed within the structure of the device and the skin. The skin is non-porous and helps to create part of the vacuum seal. When a vein, artery, potential space, or fluid filled space (Examples: epidural, subdural, or sinus space) is reached by the needle, the vacuum created in the vacuum chamber is broken and the spring is able to then propel the plunger forward. As the plunger advances it pushes the catheter into the vein, artery, potential, or fluid filled space mentioned above. In this way, a vein or artery is never pierced on both sides. The success rate of a proper insertion of an IV catheter is greatly increased. This leads to less patient discomfort and less time and anxiety in performing a proper catheter insertion.

The embodiments taught herein have been considerably simplified from prior art designs. These novel embodiments includes just two seals and one spring. There are also fewer components that make up the assembly. Furthermore, most of the parts have also been designed to be made in a simple two part mold. The necessary parts comprise a needle, a needle base, a catheter, a housing, a plunger, a spring, two seals and a cap. As will be shown, the needle base could be integrated into the housing further reducing the part count. The improved design is significantly cheaper to manufacture and the reduction in parts increases the reliability of the device. The simplicity in design makes this device feasible to compete against the current products on the market.

Another novel aspect of this invention is that the plunger not only acts a piston advancing the catheter but it also acts as a needle guard once the catheter has been inserted. This novel combination of structure further helps to reduce parts and simplify the design.

Figure 1:
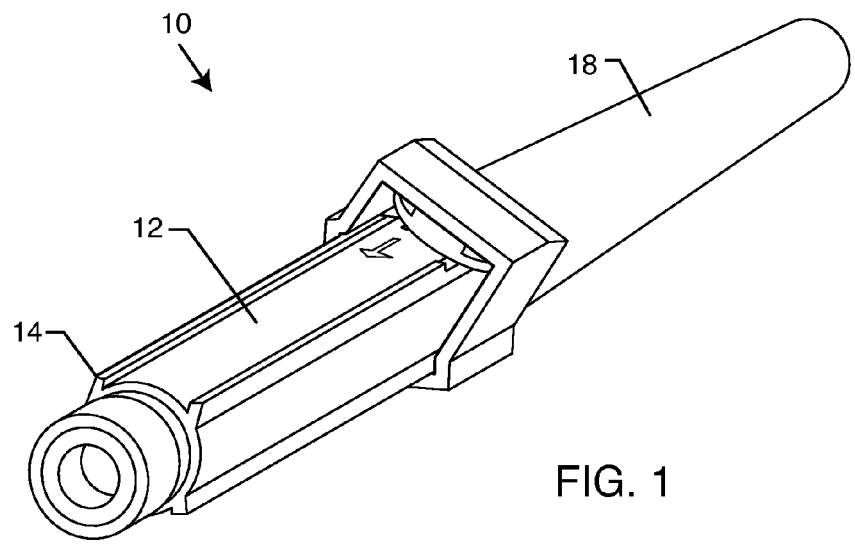
FIG. 1 is a perspective view of an exemplary catheter insertion device of the present invention.
Figure 2:
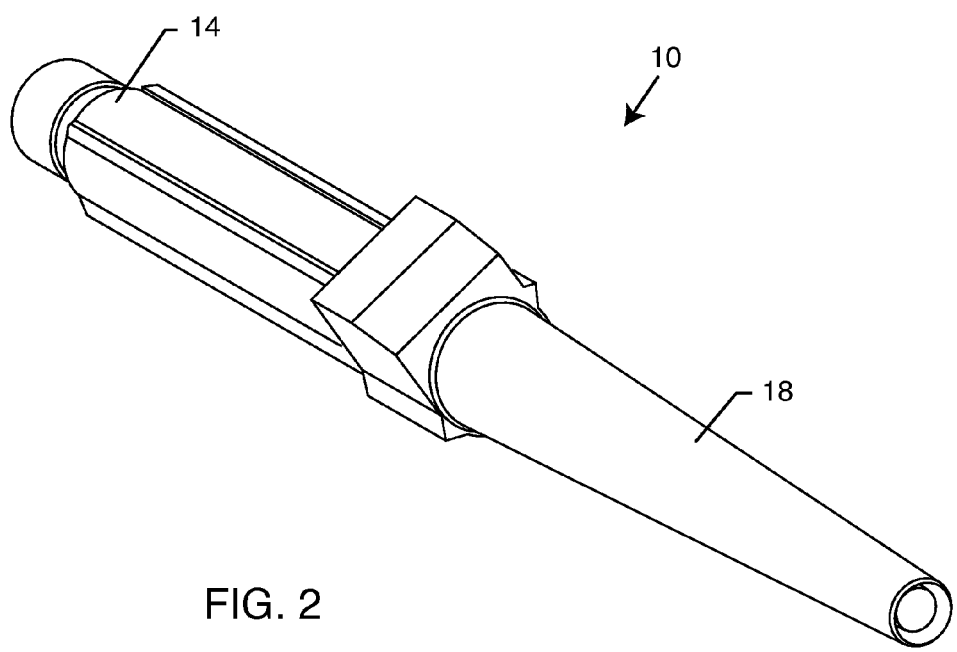
FIG. 2 is another perspective view of the exemplary embodiment of FIG. 1.
Figure 5:
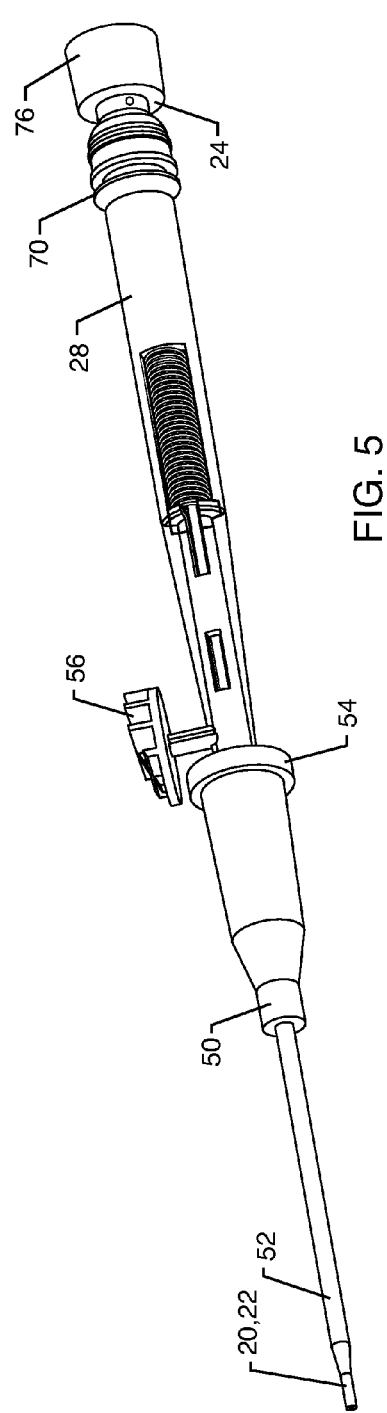
FIG. 5 is a perspective view similar to FIG. 4 now with the housing removed.
Figure 6:
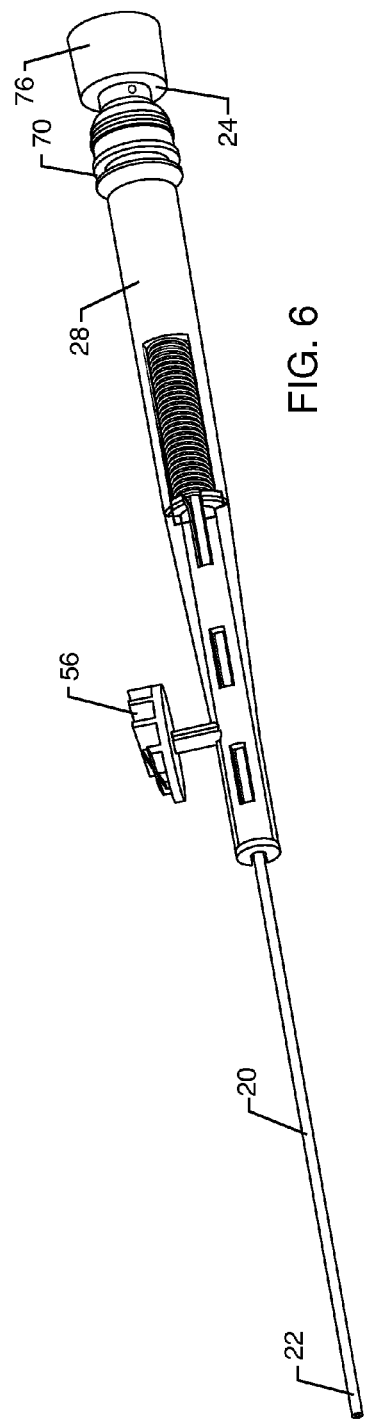
FIG. 6 is a perspective view similar to FIG. 5 now with the catheter removed.

As shown in FIGS. 1-16, an exemplary embodiment of a catheter insertion device 10 has a generally hollow housing 12 having a closed base end 14 opposite an open distal end 16. As shown in FIGS. 1-3 a cap 18 is shown connected to the distal end 16. When the device is about to be used, the cap 18 is removed which exposes the hollow needle 20, as is seen in FIG. 4.

Figure 11:
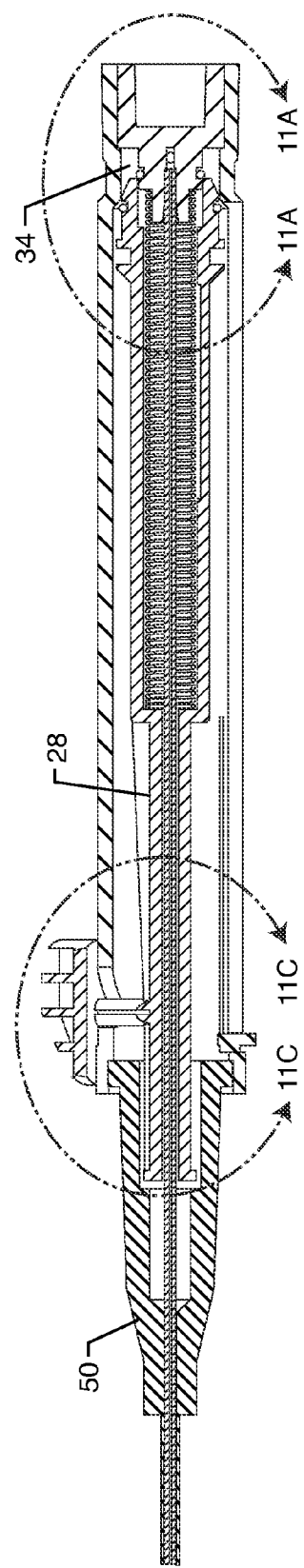
FIG. 11 is sectional side view of the structure of FIG. 4 taken along lines 11-11
Figure 11A:
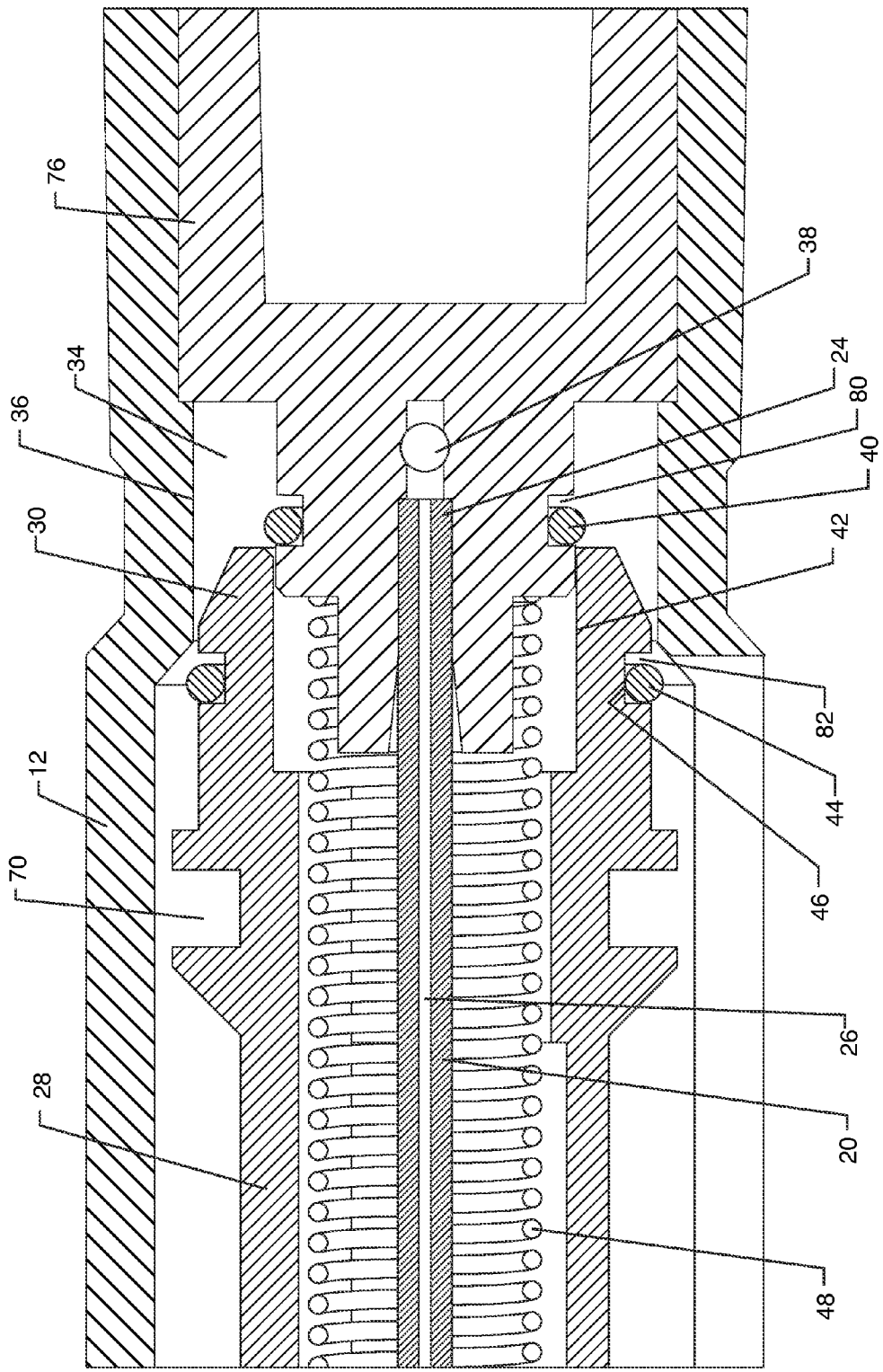
FIG. 11A is an enlarged view of the section taken along lines 11A-11A from FIG. 11 showing the plunger in the stored position.

The hollow needle 20 has a distal skin-piercing end 22 opposite a proximal needle end 24. The proximal needle end 24 is non-movably attached to the closed base end 14 of the generally hollow housing 12 where the proximal needle end 24 is disposed within the generally hollow housing 12, as is best shown in FIG. 11A. In these embodiments, the needle's proximal needle end 24 is inserted into a proximal base end/needle base 76. The needle base 76 may be formed as part of the closed base end 14 of the housing 12 or may be a separate part as shown herein. As shown in FIGS. 14 and 14A the proximal base end/needle base 76 has a hole 78 for the proximal needle end 24 to be secured and fixedly attached. The needle base 76 is then permanently secured within the closed base end 14 of the housing 12 to then close it. The needle base 76 may be glued or bonded to the housing 12, or alternatively could be an interference fit or even as another alternative they could be screwed into each other with a male-female threaded ends. As shown herein, the needle base 76 is constructed as a separate part because it is easier to then place the aperture 38 within the needle base 76. This aperture 38 is an important aspect of the invention as it creates a path for the vacuum to be communicated during operation of the device. Furthermore, the proximal needle end 24 could be glued, bonded, molded, screwed or attached to the needle base 76/closed base end 14 of the housing 12 by an interference fit.

As shown in FIG. 4, the distal skin-piercing end 22 of the hollow needle 20 extends beyond the open distal end 16 of the generally hollow housing 12. The hollow needle 20 defines a channel 26 in fluidic or pneumatic communication between the distal skin-piercing end 22 and the proximal needle end 24. A plunger 28 is then slidably disposed over at least a portion of the hollow needle 20. The plunger 28 slides along the needle 20, or it can be said that the plunger 28 translates or moves along the needle. As shown herein, the plunger 28 can also rotate about the needle 20, yet rotation is not a necessary requirement. For instance, the plunger 28 and housing 12 could be constructed in a square or rectangular manner as compared to the circular version shown herein. It is simply easier to manufacture and assemble the circular version as orientation in assembly and use is not as critical.

Figure 11B:
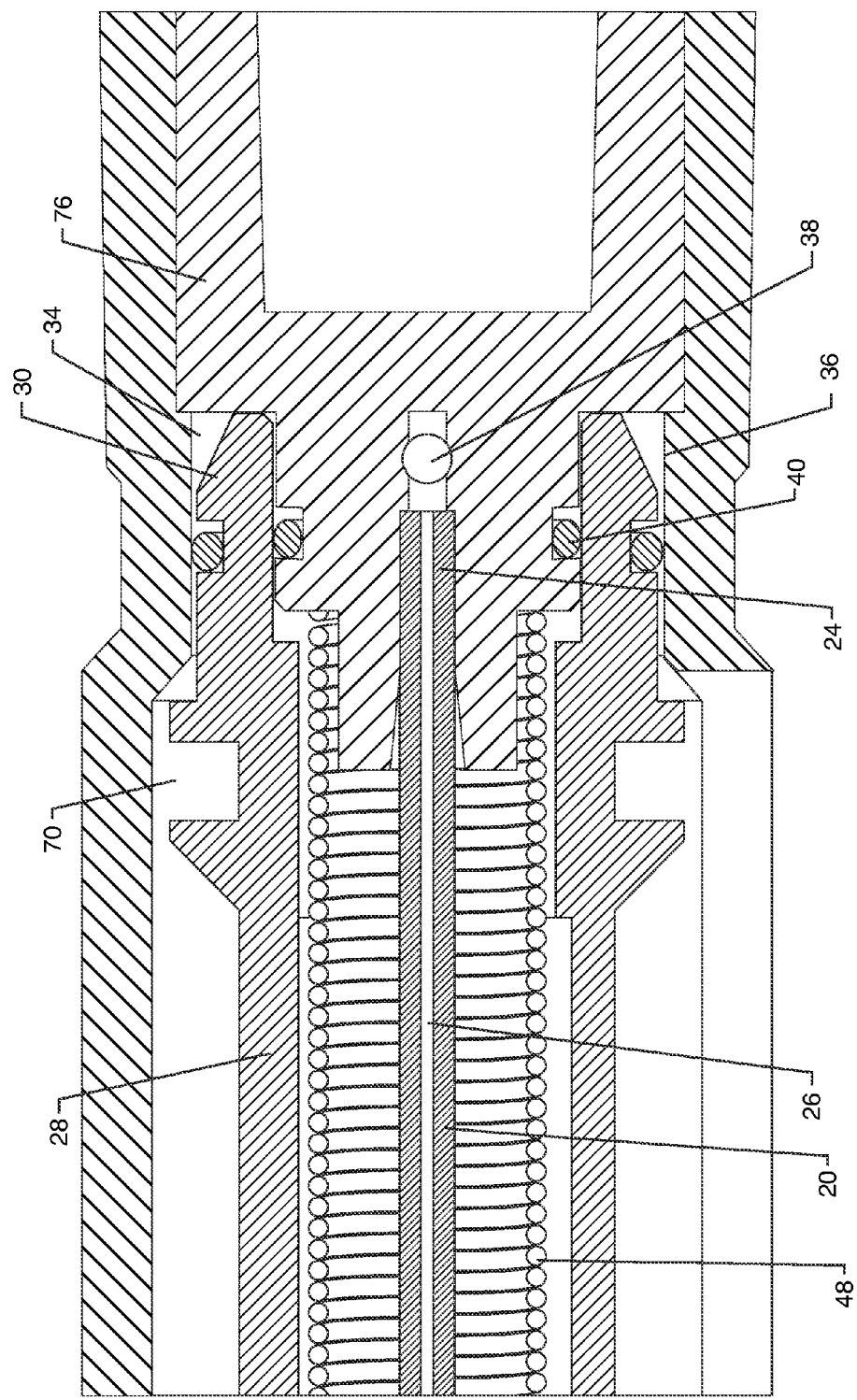
FIG. 11B is a view similar to FIG. 11A now showing the plunger in the armed position.

The plunger 28 includes a plunger proximal chamber end 30 opposite a plunger distal end 32. The distal skin-piercing end 22 of the hollow needle 20 extends through the plunger distal end 32. As best shown in FIGS. 11A and 11B, an expandable chamber 34 is at least partially formed by the plunger proximal chamber end 30 and at least an inside surface 36 of the housing 12 and the closed based end 76 of the generally hollow needle 20. The expandable chamber 34 is in fluidic or pneumatic communication with the channel 26 of the hollow needle 20 through the proximal needle end 24, where the aperture/hole 38 may be located. The expandable chamber 34 is configured to increase in volume as the plunger 28 moves towards the distal skin-piercing end 22 of the hollow needle 20.

A first seal 40 is attached to either an inside surface 42 of the plunger 28 or the generally hollow housing 12/needle base 76. A second seal 44 is attached to either an outside surface 46 of the plunger 28 or the generally hollow housing 12. The first seal 40 is configured to seal between the inside surface 42 of the plunger and the generally hollow housing 12/needle base 76 when the plunger 28 is at its furthest proximal position and the second seal 44 is configured to seal between the outside surface 46 of the plunger and the generally hollow housing 12 when the plunger 28 is at its furthest proximal position. As shown herein, each seal may be an O-ring or other suitable structure, whether it be a rectangular, square or circular in section. To keep each seal in its required position, each seal has been assembled into a channel. For instance, the needle base 76 has a circumferential channel 80 that captures the first seal 40. The plunger 28 also has a circumferential channel 82 for capturing the second seal 44. As can be understood by those skilled in the art, the channels 80 and 82 could be formed on the opposing surface and the device would function similarly. Furthermore, the channels could be removed and the device would function similarly.

A spring 48 is mechanically engaged between the generally hollow housing 12/needle base 76 and the plunger 28. The spring 48 biases the plunger 28 towards the distal skin-piercing end 22 of the hollow needle 20. A catheter 50 is slidably disposed over at least a second portion of the hollow needle 20 where the distal skin-piercing end 22 of the hollow needle 20 extends through a distal insertion end 52 of the catheter 50. The catheter 50 includes the distal insertion end 52 opposite a proximal connection end 54, where the proximal connection end 54 of the catheter 50 is configured to be disposed next to the plunger distal end 32.

Figure 16:
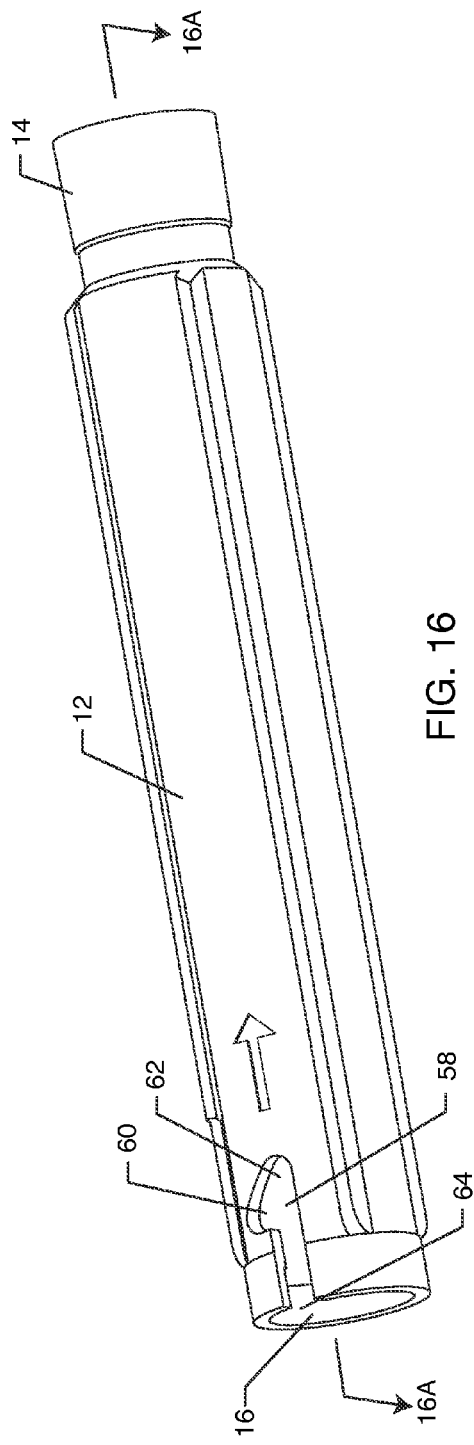
FIG. 16 is a perspective view of an exemplary housing of the structure of FIGS. 1-15.

A button 56 is non-movably attached to the plunger 28 and extends outside of the generally hollow housing 12. The housing 12 may include a J-shaped slot 58, where the button 56 is configured to be moveable within the J-shaped slot 58 between a stored position 60, an armed position 62 and an extended position 64. This is best seen in FIG. 16. The stored position 60 is when the button is located at a lower end of the J-shaped slot 58. The armed position 62 is when the plunger 28 is moved to its furthest proximal position at the very bottom of the J-shaped slot. The extended position 64 is when the plunger 28 is moved to its furthest distal position.

One skilled in the art will understand that the button 56 may be removed altogether or even relocated onto another part while the invention would still be configured to function properly. For instance, the button 56 may be integrated onto the housing 12 and still control the movement of the plunger 28. Furthermore, the shape of the J-shaped slot 58 may also be modified or even removed. For instance, the plunger 28 may be preloaded during manufacture. The user would then press a button 56 or engage some sort of release once the distal skin-piercing end 22 has penetrated the patient's skin. Therefore, in this embodiment the slot has been completely removed.

When the cap 18 is on the device 10 the button 56 has been moved to the stored position 60. This means that the spring 48 has been compressed and an internal bias is already present within the device. The stored position 60 corresponds to the sectional view of FIG. 11A. It is important to note that in the stored position 60, the seals 40 and 44 are not in contact with two surfaces. The structure has been designed such that the seals are only captured within their respective channels. This is important because the seals could create an amount of static friction or stickiness that prevents the device from operating correctly. It was discovered that the seals tends to flow like a fluid even though they are made from rubber or rubberlike materials. If placed between two surfaces for a long period of time they tend to stick and hold the two surfaces together. This would impede proper operation of the device 10 if they were stored for a long period of time between two surfaces. Therefore, in the stored position 60, the seals are not sealing to their second surface but rather are captured in their primary channels ready to be used as a seal.

FIG. 11B then corresponds to the armed position 62 where the cap 18 is removed and the plunger 28 has been retracted by the user through the button 56. The user can then insert the distal skin-piercing end 22 of the needle 20 and let go of the button 56. As can be seen in FIG. 11B, the expandable chamber 34 has substantially zero-volume or very little volume. The seals 40 and 44 help to create and define the volume of the expandable chamber 34. Air or fluid is in communication, meaning it can flow freely, within the channel 26 of the needle 20 through the aperture 38 in the needle base 76 and to the expandable chamber 34.

As the user advances the needle 20 within the tissue of the patient the distal skin-piercing end 22 will eventually puncture into a vein or artery. When this happens, blood, fluid or air is able to then flow into the channel 26 and allow the expandable chamber 34 to expand. This means then that the plunger 28 is advancing forward. The spring 48 is now able to propel the plunger 28 forward a significant distance because the button 56 is able to slide to the extended position. The top of the J-shaped slot 58 is open, meaning the button 56 can pass through and keep moving forward. The plunger 28 is propelled forward which pushes the catheter 50 forward and into the vein or artery. Then the user can then push the soft catheter 50 all the way in as they withdraw the device 10 and leave the catheter 50 inserted into the patient.

The catheter 50 has a very flexible distal insertion end 52 that is designed to remain within the vein or artery. The proximal connection end 54 of the catheter 50 can then be connected to various other drug delivery devices or sample extraction devices as needed by the medical practitioner.

Figure 11C:
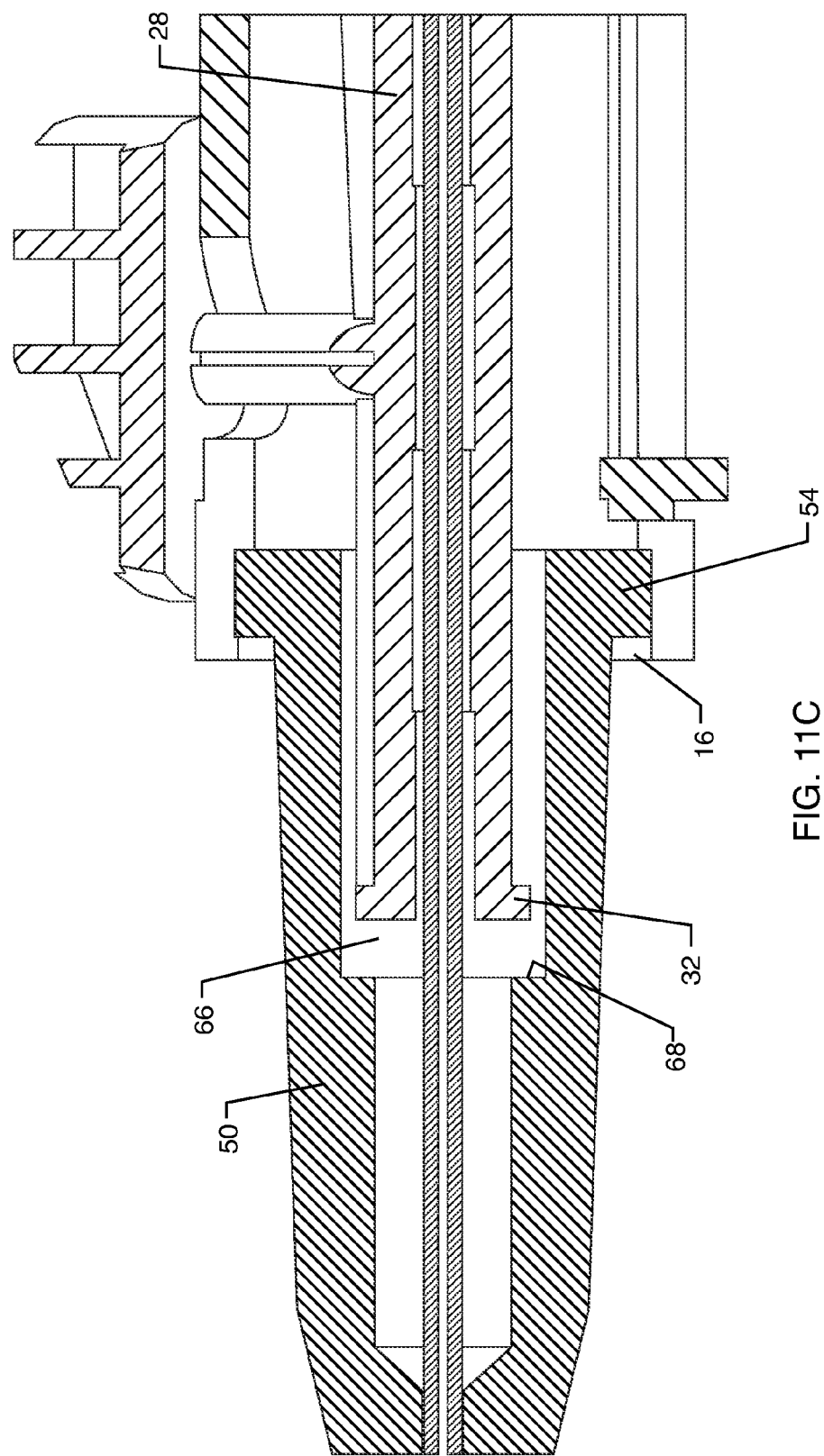
FIG. 11C is an enlarged view of the section taken along lines 11C-11C from FIG. 11.

Referring now to FIG. 11C, it is noted that in the armed position 62 there is a small gap 66 which is created between a catheter inner surface 68 and the plunger distal end 32. This gap 66 is important as it creates a space for the plunger 28 to start movement before it engages to the catheter 50. Momentum of the moving components is preferred for the device to operate optimally. Unrestricted movement is created after the vacuum in the expandable chamber 34 is broken. The plunger 28 is able to propel forward by the spring 48 and create momentum during the gap 66. Then when the plunger 28 strikes the catheter's inner surface 68 it can propel the catheter 50 forward. It is understood by those skilled in the art that the design could be changed where the plunger 28 hits the catheter 50 at a different location, such as at the proximal connection end 54 of the catheter 50.

As can be seen in FIG. 11C, the catheter 50 is loosely held at its proximal connection end 54 to the open distal end 16 of the housing 12. This is to make sure the catheter 50 does not slide and fall off the needle 20 when the cap 18 is removed. This also is used to prevent movement of the catheter 50 towards the closed base end 14 of the housing 12 when the plunger 28 is retracted into the armed position 62.

Figure 10:
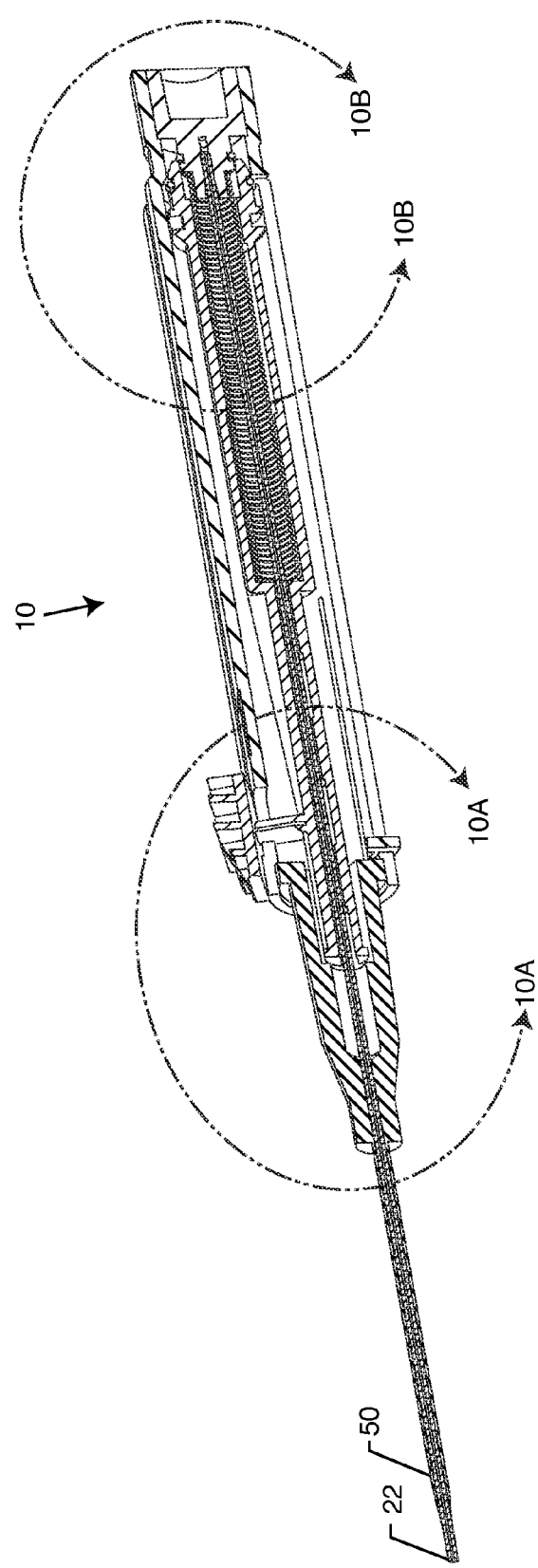
FIG. 10 is a sectional perspective view taken along lines 10-10 from FIG. 4.
Figure 10A:
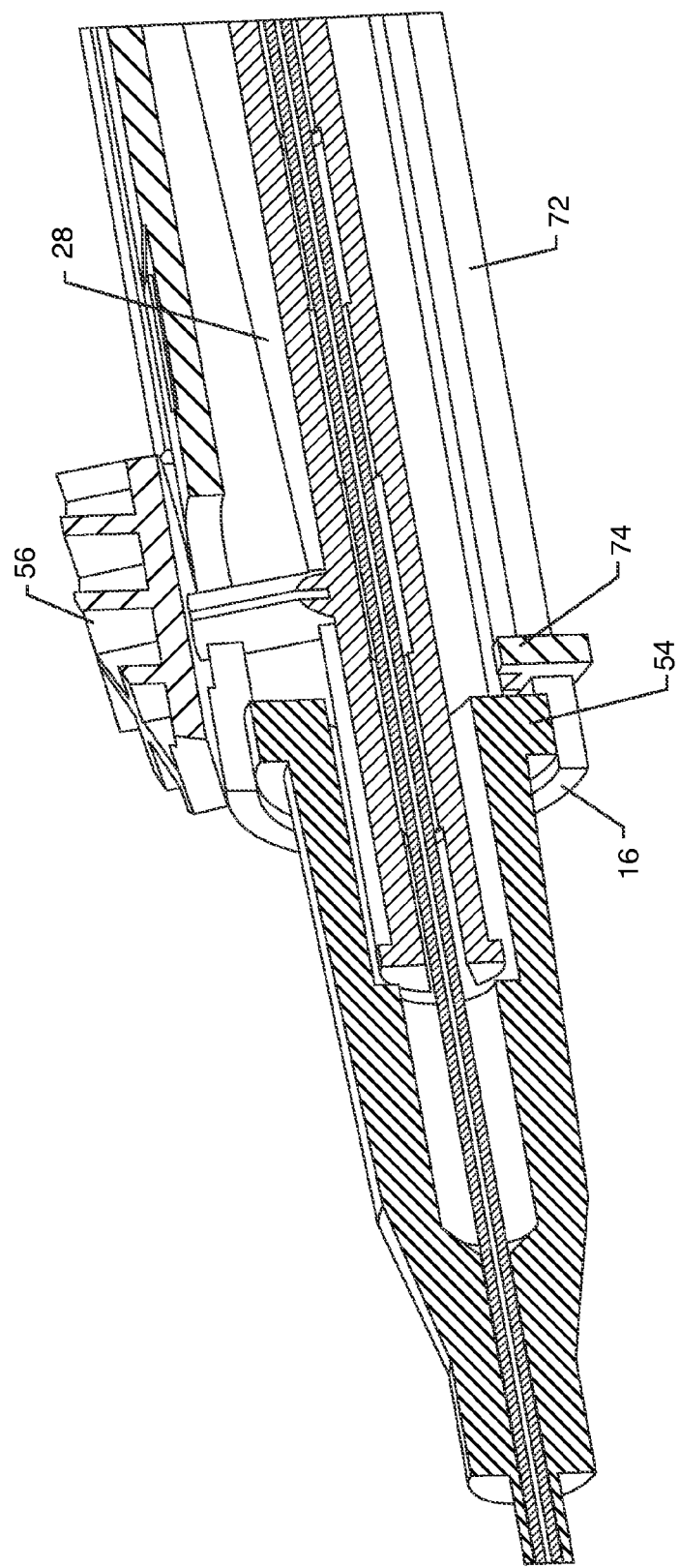
FIG. 10A is an enlarged view of the section taken along lines 10A-10A from FIG. 10.
Figure 10B:
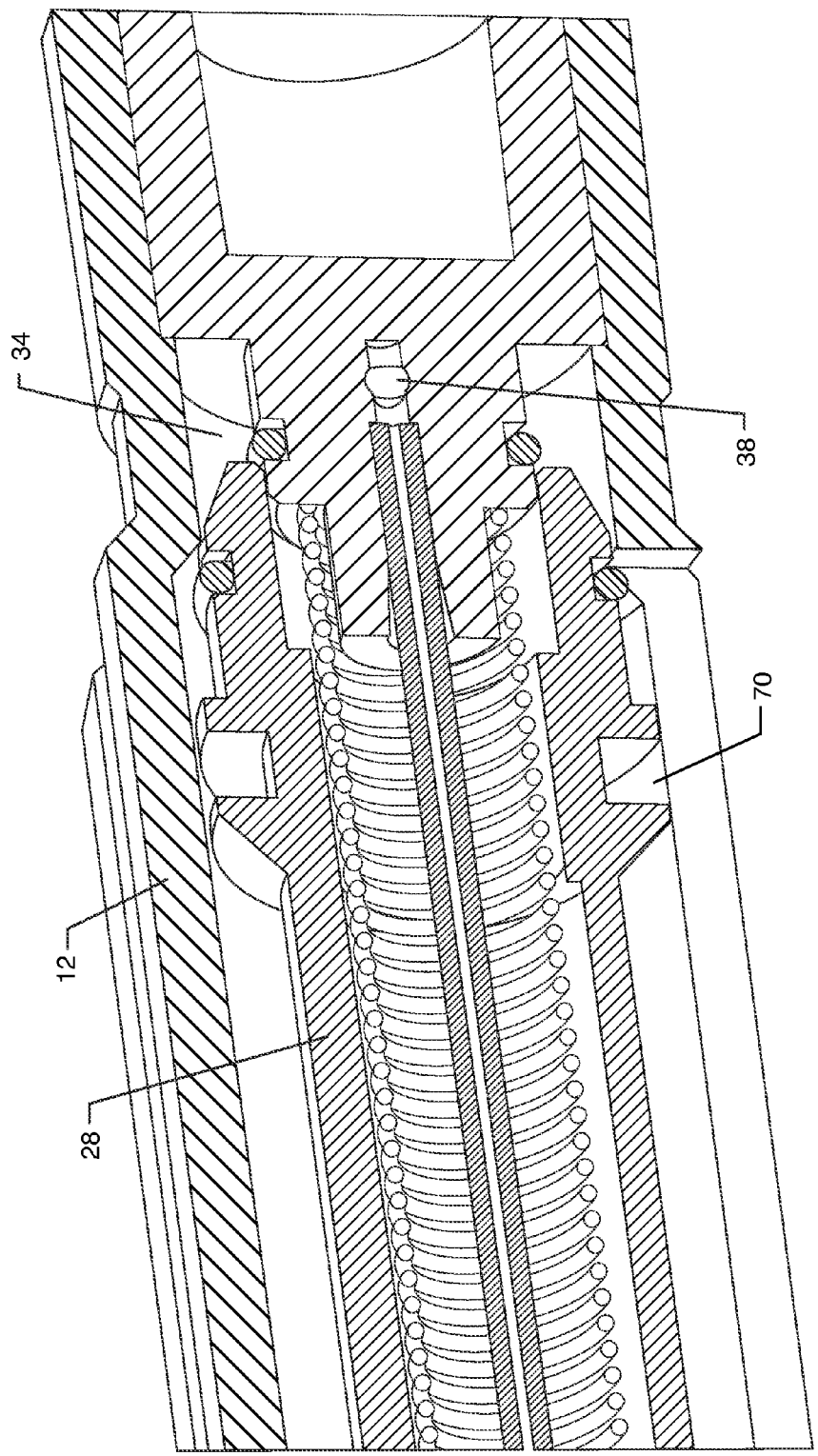
FIG. 10B is an enlarged view of the section taken along lines 10B-10B from FIG. 10.

As best seen in FIGS. 10A and 10B, the plunger 28 may have a circumferential recess 70 allowing the plunger 28 to double in function as a needle guard. The generally hollow housing 12 has a needle guard flexure 72 having a distal engagement tip 74. When the plunger 28 is in the extended position 64 the distal engagement tip 74 of the housing 12 is captured within the circumferential recess 70 of the plunger 28. The plunger 28 is then fixedly secured in relation to the hollow needle 12 and the housing 12. The plunger distal end 32 is positioned beyond and covers the distal skin-piercing end 22 of the hollow needle 20.

It will be appreciated that to make the device 10 work properly there must be an optimum balance between all the forces acting within this novel structure. The spring rate must be formed such that it is enough the advance the plunger 28 forward when an artery or vein is reached, but not too strong that it prematurely overpowers the vacuum in the expandable chamber 34 and prematurely deploys the catheter 50. Also, the frictional force of the seals 40, 44 must not be too high that the spring 48 cannot advance the plunger 28 forward when an artery, vein, potential space, or fluid filled cavity is reached. This is why the J-shaped slot 58 allows the seals 40 and 44 to be free during storage in the stored position 60 and then engaged in the armed position 62. This prevents the seals from flowing into the abutting surfaces and sticking. For instance, if the seals were engaged during storage, the longer the product was stored the more the seals would stick. Due the delicate balances of forces for the invention to work properly, storing the seals in the armed position or a similar position could ruin the functionality of the catheter insertion device 10.

During testing, a preferred spring used herein had a calculated spring rate when extended of about 0.140 lbs./inch. A calculated maximum safe load was about 0.378 lbs. at 0.801 compressed (solid) height which corresponded to about 2.699 inches of travel. More specifically, another spring used herein had an outer diameter of 0.120 inches with a 0.009 inch thickness of music wire with about a 3.50 inch free length. The spring had about 97.54 total coils which is about a 0.0364 pitch. The spring rate of this preferred spring was 0.0628 lbs./inch. The ends of the spring were closed and not ground. The finish was a plain finish. One skilled in the art will understand that many variations from these preferred spring embodiments are possible for the device 10. The values disclosed herein could range for example by plus or minus ten percent, or even plus or minus twenty-five percent. For example, one skilled in the art could use springs rated at less than 0.50 lbs./inch, or preferably less than 0.25 lbs./inch, or preferably less than 0.125 lbs./inch. Also as an example, the springs may have an outer diameter less than 0.25 inches, or preferably less than 0.125 inches.

A novel feature of the present invention is the simplicity in the design. This structure only requires the use of just one spring 48. Furthermore, there are only two seals 40 and 44 used to create the vacuum within the expandable chamber 34. Furthermore, the plunger 28 also acts as a needle guard further simplifying the structure.

Figure 16A:
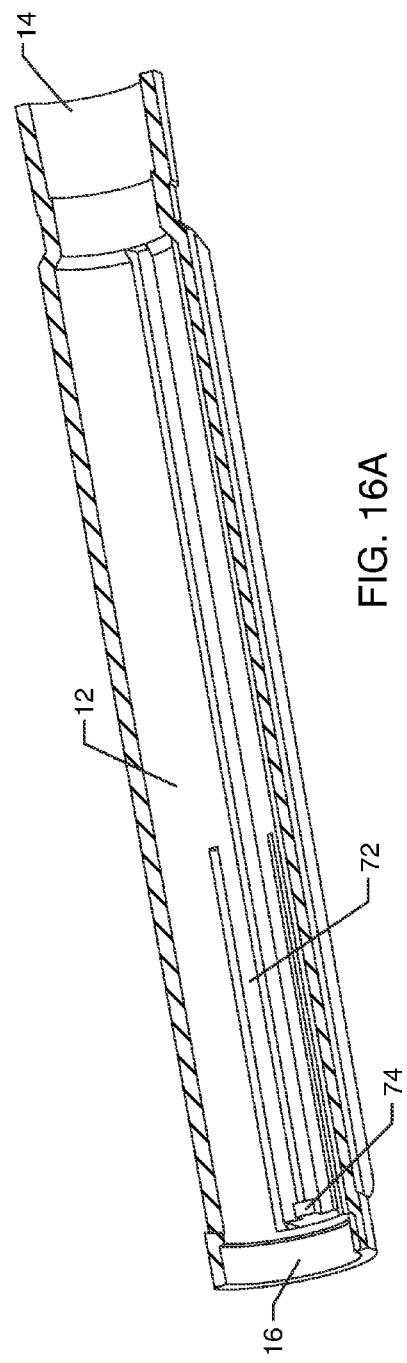
FIG. 16A is a sectional view taken along lines 16A-16A from FIG. 16.

As can be best seen in FIGS. 16 and 16A, the housing has been formed such that the J-shaped slot 58 is formed therein and also the needle guard flexure 72 is formed therein. This simplifies the part count as extra parts are not required. As can best be seen in FIGS. 12 and 13, the plunger 28 has been formed with various slots and cutouts such that it can be made in a simple two part mold. Furthermore, the button 56 and the circumferential recess 70 has been integrated within to further simply the design by reducing the part count.

Although several embodiments have been described in detail for purposes of illustration, various modifications may be made to each without departing from the scope and spirit of the invention. Accordingly, the invention is not to be limited, except as by the appended claims.

What is claimed is:

1. A catheter insertion device, comprising:
    a hollow needle having a distal skin-piercing end opposite a proximal base end, the hollow needle defining a channel in fluidic or pneumatic communication between the distal skin-piercing end and the proximal base end;
    a plunger slidably disposed over at least a portion of the hollow needle, where the distal skin-piercing end of the hollow needle extends through a distal end of the plunger;
    a spring mechanically engaged between at least a portion of the proximal base end of the hollow needle and a portion of the plunger, the spring biasing the plunger towards the distal skin-piercing end of the hollow needle;
    a catheter slidably disposed over at least a second portion of the hollow needle where the distal skin-piercing end of the hollow needle extends through a distal insertion end of the catheter, the catheter comprising the distal insertion end opposite a proximal connection end, where a surface of the catheter contacts the distal end of the plunger during catheter insertion; and
    an expandable chamber having a first opening in fluidic or pneumatic communication with the channel of the hollow needle, the expandable chamber at least partially formed by the proximal base end of the hollow needle and a proximal end of the plunger, the expandable chamber configured to increase in volume as the plunger moves towards the distal skin-piercing end of the hollow needle.

2. The catheter insertion device of claim 1, including a housing attached to the proximal base end of the hollow needle.

3. The catheter insertion device of claim 2, including a first circumferential seal of the expandable chamber disposed about the proximal base end of the hollow needle, the first circumferential seal configured to seal the proximal base end to the plunger when the plunger is moved to its furthest proximal position.

4. The catheter insertion device of claim 3, including a second circumferential seal of the expandable chamber disposed about the plunger, the second circumferential seal configured to seal the plunger to the housing when the plunger is moved to its furthest proximal position.

5. The catheter insertion device of claim 4, including a button non-movably attached to the plunger and extending outside of the housing.

6. The catheter insertion device of claim 5, wherein the housing includes a J-shaped slot, where the plunger moves with the button as the button is configured to be moveable within the J-shaped slot between a stored position, an armed position and an extended position, wherein the stored position comprises when the button is located at a lower end of the J-shaped slot, wherein the armed position comprises when the plunger and button are moved to their furthest proximal position, and wherein the extended position comprises when the plunger and button are moved to their furthest distal position.

7. The catheter insertion device of claim 6, wherein in the armed position a small gap is disposed between the proximal connection end of the catheter and the distal end of the plunger.

8. The catheter insertion device of claim 7, wherein the plunger comprises a circumferential recess, and wherein the housing comprises a needle guard flexure having a distal engagement tip.

9. The catheter insertion device of claim 8, wherein the first and second circumferential seals are each configured to abut only one of either the plunger or the housing when the plunger is in the extended position and stored position.

10. The catheter insertion device of claim 9, wherein the expandable chamber comprises a substantially zero volume when the plunger is in the armed position.

11. A catheter insertion device, comprising:
a generally hollow housing having a closed base end opposite an open distal end;
a hollow needle having a distal skin-piercing end opposite a proximal needle end, where the proximal needle end is non-movably attached to the closed base end of the generally hollow housing and where the proximal needle end is disposed within the generally hollow housing, wherein the distal skin-piercing end of the hollow needle extends beyond the open distal end of the generally hollow housing, where the hollow needle defines a channel in fluidic or pneumatic communication between the distal skin-piercing end and the proximal needle end;
a plunger slidably disposed over at least a portion of the hollow needle, the plunger comprising a plunger proximal chamber end opposite a plunger distal end, where the distal skin-piercing end of the hollow needle extends through the plunger distal end;
an expandable chamber at least partially formed by the plunger proximal chamber end and at least an inside surface of the closed base end of the generally hollow housing, where the expandable chamber is in fluidic or pneumatic communication with the channel of the hollow needle through the proximal needle end, where the expandable chamber is configured to increase in volume as the plunger moves towards the distal skin-piercing end of the hollow needle;
a first seal attached to either an inside surface of the plunger or the generally hollow housing, and a second seal attached to either an outside surface of the plunger or the generally hollow housing, where the first seal is configured to seal between the inside surface of the plunger and the generally hollow housing when the plunger is at its furthest proximal position and the second seal is configured to seal between the outside surface of the plunger and the generally hollow housing when the plunger is at its furthest proximal position;
a spring mechanically engaged between the generally hollow housing and the plunger, the spring biasing the plunger towards the distal skin-piercing end of the hollow needle; and
a catheter slidably disposed over at least a second portion of the hollow needle where the distal skin-piercing end of the hollow needle extends through a distal insertion end of the catheter, the catheter comprising the distal insertion end opposite a proximal connection end, where a surface of the catheter contacts the plunger distal end during catheter insertion.

12. The catheter insertion device of claim 11, including a button non-movably attached to the plunger and extending outside of the generally hollow housing.

13. The catheter insertion device of claim 12, wherein the housing includes a J-shaped slot, where the plunger moves with the button as the button is configured to be moveable within the J-shaped slot between a stored position, an armed position and an extended position, wherein the stored position comprises when the button is located at a lower end of the J-shaped slot, wherein the armed position comprises when the plunger and button are moved to their furthest proximal position, and wherein the extended position comprises when the plunger and button are moved to their furthest distal position.

14. The catheter insertion device of claim 13, wherein in the armed position a small gap is disposed between the proximal connection end of the catheter and the plunger distal end.

15. The catheter insertion device of claim 14, wherein the plunger comprises a circumferential recess, and wherein the generally hollow housing comprises a needle guard flexure having a distal engagement tip.

16. The catheter insertion device of claim 15, wherein the first and second seals are each configured to abut only one of either the plunger or the housing when the button of the plunger is in the stored or extended position.

17. The catheter insertion device of claim 16, wherein the proximal connection end of the catheter engages the open distal end of the generally hollow housing, where movement of the catheter towards the closed base end of the generally hollow housing is prevented when the plunger moves towards the closed base end of the generally hollow housing when the plunger moves from the stored position to the armed position.

18. A catheter insertion device, comprising:
an elongated hollow needle having a distal skin-piercing end opposite a proximal needle end, where the proximal needle end is non-movably fixed to a needle base, where the elongated hollow needle defines a channel in fluidic or pneumatic communication between the distal skin-piercing end and the proximal needle end;

a generally hollow housing having an open distal end opposite a housing proximal end, where the needle base is non-movably attached to the housing proximal end;

a plunger translatably disposed over at least a portion of the elongated hollow needle, where the distal skin-piercing end extends through a plunger distal end;

a spring mechanically engaged between the plunger and either the housing proximal end or the needle base, the spring configured to bias the plunger towards the distal skin-piercing end;

a catheter translatably disposed over at least a second portion of the elongated hollow needle, the catheter comprising a distal insertion end opposite a proximal connection end, where the distal skin-piercing end extends through the distal insertion end of the catheter, and where a surface of the catheter contacts the plunger distal end during catheter insertion;

an expandable chamber formed by a plunger proximal end of the plunger, an outside surface of the needle base and an inside surface of the housing proximal end, the expandable chamber varying in volume according to translational movement of the plunger;

a first seal disposed around the outside surface of the needle base; and a second seal disposed around an outside surface of the plunger.

19. The catheter insertion device of claim 18, wherein the plunger is manually moveable between a stored position and an armed position, where the armed position comprises the chamber having a substantially zero volume as the plunger is in its furthest proximal position.

20. The catheter insertion device of claim 19, wherein when the plunger is in the armed position, the first seal is disposed between the outside surface of the needle base and an inside surface of the plunger, and the second seal is disposed between the outside surface of the plunger and the inside surface of the housing proximal end.

21. A catheter insertion device, comprising:
a generally hollow housing comprising an open distal end opposite a housing base end;
a hollow needle having a distal skin-piercing end opposite a proximal needle end, the hollow needle defining a channel in fluidic or pneumatic communication between the distal skin-piercing end and the proximal needle end, where the proximal needle end is non-movably attached to the housing base end and the distal skin-piercing end of the hollow needle extends beyond the open distal end of the generally hollow housing;
a plunger slidably disposed over at least a portion of the hollow needle, the plunger comprising a plunger proximal end opposite a plunger distal end, where the distal skin-piercing end of the hollow needle extends through the plunger distal end; and
a spring mechanically engaged between the generally hollow housing and the plunger, the spring biasing the plunger towards the distal skin-piercing end of the hollow needle;
wherein an expandable chamber is defined at least partially by the plunger proximal end and an inside surface of the housing base end, where the expandable chamber is in fluidic or pneumatic communication with the channel of the hollow needle, where the expandable chamber is configured to increase in volume as the plunger moves towards the distal skin-piercing end of the hollow needle;
wherein at least a portion of the plunger movably extends out through the open distal end of the generally hollow housing.

22. The catheter insertion device of claim 21, including a first seal disposed between an outside surface of the plunger and the housing base end.

23. The catheter insertion device of claim 22, including a second seal disposed between an inside surface of the plunger and the housing base end.

24. The catheter insertion device of claim 23, including a catheter slidably disposed over at least a second portion of the hollow needle where the distal skin-piercing end of the hollow needle extends through a distal insertion end of the catheter, the catheter comprising the distal insertion end opposite a proximal connection end, where the proximal connection end of the catheter is configured to be disposed next to the plunger distal end.

25. A catheter insertion device, comprising:
a generally hollow housing comprising an open distal end opposite a housing base end:
a hollow needle having a distal skin-piercing end opposite a proximal needle end, the hollow needle defining a channel in fluidic or pneumatic communication between the distal skin-piercing end and the proximal needle end, where the proximal needle end is non-movably attached to the housing base end and the distal skin-piercing end of the hollow needle extends beyond the open distal end of the generally hollow housing;
a plunger slidably disposed over at least a portion of the hollow needle, the plunger comprising a plunger proximal end opposite a plunger distal end, where the distal skin-piercing end of the hollow needle extends through the plunger distal end; and
a spring mechanically engaged between the generally hollow housing and the plunger, the spring biasing the plunger towards the distal skin-piercing end of the hollow needle;
wherein an expandable chamber is defined at least partially by the plunger proximal end and an inside surface of the housing base end, where the expandable chamber is in fluidic or pneumatic communication with the channel of the hollow needle, where the expandable chamber is configured to increase in volume as the plunger move towards the distal skin-piercing end of the hollow needle;
wherein the spring mechanically engaged between the generally hollow housing and the plunger is the only spring in the catheter insertion device.

26. A catheter insertion device, comprising:
a generally hollow housing comprising an open distal end opposite a housing base end;
a hollow needle having a distal skin-piercing end opposite a proximal needle end, the hollow needle defining a channel in fluidic or pneumatic communication between the distal skin-piercing end and the proximal needle end, where the proximal needle end is non-movably attached to the housing base end and the distal skin-piercing end of the hollow needle extends beyond the open distal end of the generally hollow housing;
a plunger slidably disposed over at least a portion of the hollow needle, the plunger comprising a plunger proximal end opposite a plunger distal end, where the distal skin-piercing end of the hollow needle extends through the plunger distal end; and a spring mechanically engaged between the generally hollow housing and the plunger, the spring biasing the plunger towards the distal skin-piercing end of the hollow needle;

wherein an expandable chamber is defined at least partially by the plunger proximal end and an inside surface of the housing base end, where the expandable chamber is in fluidic or pneumatic communication with the channel of the hollow needle, where the expandable chamber is configured to increase in volume as the plunger move towards the distal skin-piercing end of the hollow needle;

wherein a catheter is advanced by the plunger during catheter insertion.

* * * * *